United States Patent
Franzke et al.

(10) Patent No.: US 10,619,125 B2
(45) Date of Patent: Apr. 14, 2020

(54) PROCESS FOR MAKING MIXTURES OF ENANTIOMERS OF MGDA AND GLDA

(71) Applicant: BASF SE, Ludwigshafen (DE)

(72) Inventors: Constanze Franzke, Duesseldorf (DE); Marta Reinoso Garcia, Dossenheim (DE); Robert Baumann, Mannheim (DE); Thomas Greindl, Kallstadt (DE)

(73) Assignee: BASF SE, Ludwigshafen (DE)

( * ) Notice: Subject to any disclaimer, the term of this patent is extended or adjusted under 35 U.S.C. 154(b) by 117 days.

(21) Appl. No.: 15/554,466

(22) PCT Filed: Mar. 2, 2016

(86) PCT No.: PCT/EP2016/054375
§ 371 (c)(1),
(2) Date: Aug. 30, 2017

(87) PCT Pub. No.: WO2016/142228
PCT Pub. Date: Sep. 15, 2016

(65) Prior Publication Data
US 2018/0237728 A1    Aug. 23, 2018

(30) Foreign Application Priority Data

Mar. 12, 2015 (EP) .................................... 15158841

(51) Int. Cl.
| C11D 3/33 | (2006.01) |
| C07C 227/18 | (2006.01) |
| C07C 253/00 | (2006.01) |
| C07C 253/06 | (2006.01) |

(52) U.S. Cl.
CPC .............. *C11D 3/33* (2013.01); *C07C 227/18* (2013.01); *C07C 253/00* (2013.01); *C07C 253/06* (2013.01)

(58) Field of Classification Search
CPC ....................................................... C11D 3/33
See application file for complete search history.

(56) References Cited

U.S. PATENT DOCUMENTS

| 2009/0075855 A1* | 3/2009 | Gibis ........................ C11D 3/33 510/224 |
| 2010/0222610 A1* | 9/2010 | Boonstra ............... C07C 227/26 562/561 |
| 2010/0324334 A1* | 12/2010 | Boonstra ............... C07C 227/26 562/554 |
| 2011/0017239 A1* | 1/2011 | VanLoyen ............ C11D 3/3769 134/25.2 |
| 2012/0142964 A1* | 6/2012 | Lammkers ............ C07C 229/24 562/571 |
| 2012/0202720 A1 | 8/2012 | de Wolf et al. |
| 2012/0248370 A1* | 10/2012 | Oftring ................. C07C 227/26 252/182.12 |
| 2012/0283473 A1* | 11/2012 | Oftring ................. C07C 227/42 562/571 |
| 2013/0012425 A1 | 1/2013 | Jefferis et al. |
| 2013/0129804 A1* | 5/2013 | Schweinsberg ...... A01N 25/008 424/409 |

FOREIGN PATENT DOCUMENTS

| DE | 198 19 187 A1 | 11/1999 |
| EP | 0 851 023 A2 | 7/1998 |
| WO | WO 2010/139755 A1 | 12/2010 |
| WO | WO 2011/076769 A1 | 6/2011 |
| WO | 2011080540 * | 7/2011 |
| WO | WO 2011/080540 A1 | 7/2011 |
| WO | WO 2011/100344 A1 | 8/2011 |
| WO | WO 2012/080463 A1 | 6/2012 |
| WO | WO 2012/150155 A1 | 11/2012 |
| WO | WO 2013/056863 A1 | 4/2013 |
| WO | WO 2014/090942 A1 | 6/2014 |
| WO | WO 2014/090943 A1 | 6/2014 |
| WO | WO 2014/184280 A1 | 11/2014 |
| WO | WO 2014/191198 A1 | 12/2014 |
| WO | WO 2014/191199 A1 | 12/2014 |
| WO | WO 2015/032447 A1 | 3/2015 |
| WO | WO 2015/032451 A1 | 3/2015 |
| WO | WO 2015/036324 A1 | 3/2015 |

OTHER PUBLICATIONS

International Search Report dated May 27, 2016 in PCT/EP2016/054375.

* cited by examiner

*Primary Examiner* — Charles I Boyer
(74) *Attorney, Agent, or Firm* — Oblon, McClelland, Maier & Neustadt, L.L.P.

(57) ABSTRACT

Process for preparation of a mixture of methyl glycine diacetic acid (MGDA) or its respective mono-, di-, trialkali metal salt or its respective mono-, di- or tri-ammonium salt or mixtures thereof, and glutamic acid diacetic acid (GLDA) or its respective mono-, di-, tri-, or tetra-alkali metal or mono-, di-, tri- or tetra-ammonium salt or mixtures thereof, wherein said process com-prises the steps of: (a) dissolution in water of (a1) alanine in its L- or D-enantiomeric form or its respective monoalkali metal salt or mixtures thereof, and (a2) glutamic acid as L- or D-enantiomer or its respective mono-, or dialkali metal or mixtures thereof, wherein the molar ratio of alanine to glutamic acid is in the range of from 1:9 to 9:1, (b) converting the mixture obtained in step (a) with formaldehyde and hydrocyanic acid or alkali metal cyanide to the corresponding dinitriles, (c) saponification of the dinitriles resulting from step (b).

15 Claims, No Drawings

PROCESS FOR MAKING MIXTURES OF ENANTIOMERS OF MGDA AND GLDA

This application is a National Phase of PCT/EP2016/054375, which was filed on Mar. 2, 2016. This application is based upon and claims the benefit of priority to European Application No. 15158841.5, which was filed on Mar. 12, 2015.

The present invention is directed towards a mixture of L- and D-enantiomers of methyl glycine diacetic acid (MGDA) or its respective mono-, di- or trialkali metal or mono-, di- and triammonium salt or mixtures thereof and L- and D-enantiomers of glutamic acid diacetic acid (GLDA) or its respective mono-, di-, tri-, or tetraalkali metal or mono-, di-, tri- or tetraammonium salt or mixtures thereof, said mixture containing predominantly the respective L-isomer with an enantiomeric excess (ee) in the range of from 10 to 95%.

In another aspect the present invention is direct towards a process for preparation of a mixture of methyl glycine diacetic acid (MGDA) or its respective mono-, di-, or trialkali metal salt or its respective mono-, di- or triammonium salt or mixtures thereof, and glutamic acid diacetic acid (GLDA) or its respective mono-, di-, tri-, or tetraalkali metal or mono-, di-, tri- or tetraammonium salt or mixtures thereof, wherein said process comprises the steps of
(a) dissolution in water of
  (a1) alanine in its L- or D-enantiomeric form or its respective monoalkali metal salt or mixtures thereof, and
  (a2) glutamic acid as L- or D-enantiomer or its respective mono-, or dialkali metal salt or mixtures thereof,
wherein the molar ratio of alanine to glutamic acid is in the range of from 1:9 to 9:1,
(b) converting the mixture obtained in step (a) with formaldehyde and hydrocyanic acid or alkali metal cyanide to the corresponding dinitriles,
(c) saponification of the dinitriles resulting from step (b).

Another aspect of the present invention refers to a process for making a mixture of methyl glycine diacetic acid (MGDA) and glutamic acid diacetic acid (GLDA) or their respective mono-, di-, or trialkali metal salt or its respective mono-, di- or triammonium salt or mixtures thereof.

Chelating agents such as methyl glycine diacetic acid (MGDA) or its respective mono-, di- or tri-alkali metal or mono-, di- and triammonium salt or mixtures thereof and L- and D-enantiomers of glutamic acid diacetic acid (GLDA) or its respective mono-, di-, tri-, or tetraalkali metal or mono-, di-, tri- or tetraammonium salt or mixtures thereof, are useful sequestrants for alkaline earth metal ions such as $Ca^{2+}$ and $Mg^{2+}$. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as granules are being applied or aqueous solutions.

Granules and powders are useful because the amount of water shipped can be neglected but for most mixing and formulation processes an extra dissolution step is required.

Many industrial users wish to obtain complexing agents in aqueous solutions that are as highly concentrated as possible. The lower the concentration of the requested complexing agent the more water is being shipped. Said water adds to the costs of transportation, and it has to be removed later. Although about 40% by weight solutions of the trisodium salt of MGDA and up to 47% by weight solutions of the tetrasodium salt of GLDA can be made and stored at room temperature, local or temporarily colder solutions may lead to precipitation of the respective complexing agent, as well as nucleating by impurities. Said precipitations may lead to impurities or inhomogeneity during formulation.

Highly concentrated aqueous solutions of MGDA and of GLDA can be made under certain circumstances. However, their viscosity in many cases leaves room for improvement. Aqueous solutions of MGDA have extremely low a viscosity, and in many operations a higher viscosity is desirable, e.g. in order to avoid splashing of such solutions during processing. On the other hand, highly concentrated aqueous solutions of GLDA at ambient temperature exhibit a high viscosity. Simple combinations of GLDA and MGDA do not solve the problem.

It can be tried to increase the solubility of chelating agents by adding a solubilizing agent, for example a solubility enhancing polymer or a surfactant. However, many users wish to be flexible with their own detergent formulation, and they wish to avoid polymeric or surface-active additives in the chelating agent.

Additives that may enhance the solubility of the respective chelating agents may be considered but such additives should not negatively affect the properties of the respective chelating agent. However, many additives have a negative effect, or they limit the flexibility for later formulations.

WO2014/184280 discloses phosphate-free machine dishwash detergent compositions comprising 15 to 70% by weight of at least one of MGDA, GLDA and imino disuccinic acid (IDS) in combination with 0.1 to 15% by weight of a nonionic surfactant and at least on bleaching agent or enzyme.

WO2012/080463 discloses fluids suitable for treating carbonate formations containing GLDA and MGDA or their respective salts in combination with a corrosion inhibitor and a surfactant. The amount of GLDA and/or MGDA is disclosed with 5 to 30% by weight of the total weight of the fluid.

US 2012/0202720 discloses solutions comprising 10 to 30% by weight of GLDA and/or MGDA and/or their respective salts and their use in creating wormholes in carbonate reservoirs.

WO 2013/056863 discloses a machine dishwash detergent comprising an anionic surfactant comprising at least one sulfate or sulfonate group, a nonionic surfactant, and a mixture of at least one polycarboxylic acid and one compound selected from MGDA and its respective salts, GLDA and its respective salts and ethylene diaminodisuccinig acid and its salts.

WO 2014/090942 discloses salts of GLDA in the form of crystals. Additionally, a process to prepare salts of GLDA is disclosed.

WO 2014/090943 discloses salts of L-GLDA and D-GLDA with a ratio of L:D in the range between 100:0 to 50:50 in the form of crystals. Additionally, a process to make salts of GLDA is disclosed.

WO 2010/139755 discloses the preparation of chelating agents comprising the reaction of a cyanide with an amino acid and an aldehyde. The process is used for the making chelating agents selected from GLDA and aspartic acid N,N-diacetic acid.

WO 2011/076769 discloses the preparation of coated particles containing GLDA or its respective salts.

WO 2014/191199 discloses an aqueous solution free from surfactants comprising in the range of 30 to 60% by weight of a complexing agent selected from alkali metal salts of MGDA and alkali metal salts of GLDA, and in the range of 1 to 25% by weight of at least one salt of a sulfonic or of an organic acid.

WO 2014/191198 discloses an aqueous solution free from surfactants comprising in the range of 30 to 60% by weight of a complexing agent selected from alkali metal salts of MGDA and alkali metal salts of GLDA, and a special type of polymers.

The disadvantage of the prior art is solutions of environmentally friendly chelating agents with a high solids content can only be obtained in combination with additional solubilizing agents. Mixtures of GLDA and MGDA and/or its respective salts prepared by separate dissolution of MGDA and GLDA and/or its respective salts in water followed by mixing the different solutions have the disadvantage of being characterized by a higher viscosity.

It was therefore the objective of the present invention to provide a process for preparation of a highly concentrated mixture. Neither such process nor such aqueous solution should require the use of additives that negatively affect the properties of the respective complexing agent.

Accordingly, the process has been found. It is hereinafter also referred to as inventive process. Additionally, mixtures as defined at the outset have been found, hereinafter also referred to as inventive mixtures. Additionally, aqueous formulations containing said mixtures have been found.

The inventive process for preparation of a mixture of methyl glycine diacetic acid (MGDA) or its respective mono-, di-, or trialkali metal salt or its respective mono-, di- or tri-ammonium salt or mixtures thereof, and glutamic acid diacetic acid (GLDA) or its respective mono-, di-, tri-, or tetra-alkali metal or mono-, di-, tri- or tetra-ammonium salt or mixtures thereof comprises the steps of
(a) dissolution in water of
(a1) alanine in its L- or D-enantiomeric form or its respective monoalkali metal salt or mixtures thereof, and
(a2) glutamic acid as L- or D-enantiomer or its respective mono-, or dialkali metal salt or mixtures thereof,
wherein the molar ratio of alanine to glutamic acid is in the range of from 1:9 to 9:1.
(b) converting the mixture obtained in step (a) with formaldehyde and hydrocyanic acid or alkali metal cyanide to the corresponding dinitriles,
(c) saponification of the dinitriles resulting from step (b).

The term ammonium salts as used in the present invention refers to salts with at least one cation that bears a nitrogen atom that is permanently or temporarily quaternized. Examples of cations that bear at least one nitrogen atom that is permanently quaternized include tetramethylammonium, tetraethylammonium, dimethyldiethyl ammonium, and n-$C_{10}$-$C_{20}$-alkyl trimethyl ammonium. Examples of cations that bear at least one nitrogen atom that is temporarily quaternized include protonated amines and ammonia, such as monomethyl ammonium, dimethyl ammonium, trimethyl ammonium, monoethyl ammonium, diethyl ammonium, triethyl ammonium, n-$C_{10}$-$C_{20}$-alkyl dimethyl ammonium 2-hydroxyethylammonium, bis(2-hydroxyethyl) ammonium, tris(2-hydroxyethyl)ammonium, N-methyl 2-hydroxyethyl ammonium, N,N-dimethyl-2-hydroxyethylammonium, and especially $NH_4^+$.

In one embodiment of the present invention, inventive mixtures are mixtures of L- and D-enantiomers of molecules of general formula (Ia) in combination mixtures of L- and D-enantiomers of molecules of general formula (Ib)

(Ia)

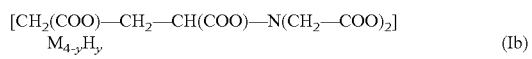
(Ib)

wherein
x is in the range of from zero to 0.5, preferably from zero to 0.25,
y is in the range of from zero to 0.5, preferably from zero to 0.25,
M is selected from ammonium, substituted or non-substituted, and potassium and sodium and mixtures thereof, preferably sodium.

Preferred are the trialkali metal salts of MGDA such as the tripotassium salts and even more preferred are the trisodium salts.

Preferred are the tetraalkali metal salts of GLDA such as the tetrapotassium salts and even more preferred are the tetrasodium salts.

In one embodiment of the present invention, the mixture consists of L- and D-enantiomers of MGDA or its respective mono-, di- or tri-alkali metal or mono-, di- or tri-ammonium salt or mixtures thereof containing predominantly the respective L-isomer with an enantiomeric excess (ee) in the range of from 10 to 95%, preferably 25 to 90%, more preferably 40 to 85%, most preferably 50 to 75%, and L- and D-enantiomers of GLDA or its respective mono-, di-, tri-, or tetra-alkali metal or mono-, di-, tri- or tetra-ammonium salt or mixtures thereof.

In embodiments where two or more compounds (Ia) are present, the ee refers to the enantiomeric excess of all L-isomers of compounds (Ia) present in the mixture compared to all corresponding D-isomers of compounds (Ia). For example, in cases wherein a mixture of the di- and trisodium salt of L-MGDA is present, the ee refers to the sum of the disodium and trisodium salt of L-MGDA with respect to the sum of the disodium and trisodium salts of D-MGDA.

The enantiomeric excess of MGDA and of its salts may be determined by measuring the polarization (polarimetry) or preferably by chromatography, for example by HPLC with a chiral column, for example with one or more cyclodextrins as immobilized phase or with a ligand exchange (Pirkle-brush) concept chiral stationary phase. Preferred is determination of the ee by HPLC with an immobilized optically active amine such as D-penicillamine in the presence of copper(II) salt.

In one aspect of the present invention, the molar ratio of MGDA to GLDA or their respective salts in the mixture is in the range of from 1:9 to 9:1, preferably 2.5:7.5 to 7.5:2.5, more preferably 4:6 to 6:4.

In one aspect of the present invention, inventive mixtures may contain less than 0.2% by weight of nitrilotriacetic acid (NTA), preferably 0.01 to 0.1% by weight.

In one embodiment of the present invention, inventive mixtures may contain in the range of from 0.1 to 10% by weight of one or more optically active impurities, at least one of the impurities being selected from iminodiacetic acid, formic acid, glycolic acid, propionic acid, acetic acid and their respective alkali metal or mono-, di- or triammonium salts, L- or D-carboxymethylalanin and its respective mono- or dialkali metal salts, L- or D-carboxymethylglutamate and its respective mono- or dialkali metal salts and the respective lactam, and optically active mono- or diamides that result from an in-complete saponification during the synthesis of the complexing agents. Preferably, the amount of optically active impurities is in the range of from 0.01 to 5% by weight, referring to the mixture of complexing agents. Even more preferably, the amount of optically active impurities is in the range of from 0.1 to 2% by weight.

In one aspect of the present invention, inventive mixtures may contain minor amounts of cations other than alkali metal or ammonium. It is thus possible that minor amounts, such as 0.01 to 5 mol-% of total chelating agent inventive mixture, based on anion, bear alkali earth metal cations such as $Mg^{2+}$ or $Ca^{2+}$, or transition metal ions such as $Fe^{2+}$ or $Fe^{3+}$ cations.

Inventive mixtures display a very good solubility, especially in water and aqueous alkali metal hydroxide solutions. Such very good solubility can be seen, e. g., in a temperature range of from zero ° C. to 40° C., in particular at room temperature and/or at zero and/or +10° C.

Another aspect of the present invention is therefore an aqueous solution of an inventive mixture, containing in the range of from 40 to 70% by weight of said inventive mixture, preferably 45 to 65% by weight, more preferably 48 to 55% by weight. Such aqueous solutions are hereinafter also being referred to as inventive solutions or solutions according to the present invention. Inventive solutions do not show amounts of precipitation or crystallization on addition of seed crystals or mechanical stress. Inventive solutions do not exhibit any visible turbidity.

In a preferred embodiment of the present invention, solutions according to the present invention are free from surfactants. Free from surfactants shall mean, in the context of the present invention, that the total contents of surfactants is 0.1% by weight or less, referring to the amount of inventive mixture. In a preferred embodiment, the term "free from surfactants" shall encompass a concentration in the range of from 50 ppm to 0.05%, both ppm and % referring to ppm by weight or % by weight, respectively, and referring to the total respective inventive solution.

In a preferred embodiment of the present invention, solutions according to the present invention are free from organic polymers. Free from organic polymers shall mean, in the context of the present invention, that the total contents of organic polymers is 0.1% by weight or less, referring to the amount of inventive mixture. In a preferred embodiment, the term "free from organic polymers" shall encompass a concentration in the range of from 50 ppm to 0.05%, both ppm and % referring to ppm by weight or % by weight, respectively, and referring to the total respective inventive solution. Organic polymers shall also include organic copolymers and shall include polyacrylates, polyethylene imines, and polyvinylpyrolidone. Organic (co)polymers in the context of the present invention shall have a molecular weight ($M_w$) of 1,000 g or more.

In a preferred embodiment of the present invention, inventive solutions do not contain major amounts of alkali metal of mono- and dicarboxylic acids such as acetic acid, propionic acid, maleic acid, acrylic acid, adipic acid, succinic acid, and the like. Major amounts in this context refer to amounts over 0.5% by weight.

In one embodiment of the present invention, inventive solutions have a pH value in the range of from 8 to 14, preferably 10.0 to 13.5.

Inventive mixtures or solutions may contain at least one inorganic basic salt selected from alkali metal hydroxides and alkali metal carbonates. Preferred examples are sodium carbonate, potassium carbonate, potassium hydroxide and in particular sodium hydroxide, for example 0.1 to 1.5% by weight. Potassium hydroxide or sodium hydroxide, respectively, may result from the manufacture of the respective inventive solution.

Furthermore, inventive mixtures as well as inventive solutions may contain one or more inorganic non-basic salts such as—but not limited to—alkali metal halide or preferably alkali metal sulphate, especially potassium sulphate or even more preferably sodium sulphate. The content of inorganic non-basic salt may be in the range of from 0.10 to 1.5% by weight, referring to the respective inventive mixture or the solids content of the respective inventive solution. Even more preferably, inventive mixtures as well as inventive solutions do not contain significant amounts of inorganic non-basic salt, for example in the range of from 50 ppm to 0.05% by weight, referring to the respective inventive mixture or the solids content of the respective inventive solution. Even more preferably inventive mixtures contain 1 to 50 ppm by weight of sum of chloride and sulphate, referring to the respective inventive mixture. The contents of sulphate may be determined, for example, by gravimetry or by ion chromatography.

Furthermore, inventive mixtures as well as inventive solutions exhibit advantageous olfactory behaviour as well as a very low tendency to colorize such as yellowing upon storage.

Furthermore, inventive mixtures as well as inventive solutions display advantageous behaviour towards bleaching agents such as sodium percarbonate, and inventive mixtures are less hygroscopic than the racemic mixture of MGDA and GLDA.

Furthermore, inventive mixtures display an improved behaviour towards strong bases such as solid potassium hydroxide or solid sodium hydroxide. When stored as a mixture with solid potassium hydroxide or solid sodium hydroxide and later formulated in water, they can be formulated as clear, non-turbid solutions with good shelve-life.

A further aspect of the present invention is a process for making inventive mixtures, hereinafter also being referred to as inventive process. The inventive process comprises the steps of (a) dissolution in water of (a1) alanine in its L- or D-enantiomeric form or its respective monoalkali metal salt or its respective monoammonium salt or mixtures thereof, and (a2) glutamic acid as L- or D-enantiomer or its respective mono-, or dialkali metal or mono- or di-ammonium salt or mixtures thereof, wherein the molar ratio of alanine to glutamic acid is in the range of from 1:9 to 9:1, (b) converting the mixture obtained in step (a) with formaldehyde and hydrocyanic acid or alkali metal cyanide to the corresponding dinitriles, (c) saponification of the dinitrile resulting from step (b).

The inventive process will be described in more detail below.

In step (a) of the inventive process, a mixture of (a1) alanine in its L- or D-enantiomeric form or its respective monoalkali metal salt or mixtures thereof, and (a2) glutamic acid as L- or D-enantiomer or its respective mono- or dialkali metal salts or mixtures thereof is dissolved in water.

The molar ratio of alanine in its L- or D-enantiomeric form or its respective monoalkali metal salt or mixtures thereof, to glutamic acid as L- or D-enantiomer or its respective mono- or dialkali metal or mixtures thereof is in the range of from 1:9 to 9:1, more preferred 2.5:7.5 to 7.5:2.5, and most preferred 4:6 to 6:4.

Of the alkali metal salts, the potassium salt is preferred and the sodium salt is even more preferred.

There are various ways to perform step (a) of the inventive process. It is possible to prepare a solid mixture of alanine in its L- or D-enantiomeric form and glutamic acid as L- or D-enantiomer and to then dissolve the mixture so obtained in water. It is preferred, though, to slurry alanine and glutamic acid or sodium glutamate in water and to then add the required amount of alkali metal hydroxide, as solid or as aqueous solution.

In one embodiment of the present invention, step (a) of the inventive process is being carried out at a temperature in the range of from 5 to 70° C., preferably in the range of from 15 to 60° C. During the performance of step (a), in many instances a raise of temperature can be observed, especially when the embodiment of slurring alanine and glutamic acid in water and to then add the required amount alkali metal hydroxide, as solid or as aqueous solution, has been chosen.

An aqueous solution of a mixture of alanine and its corresponding alkali metal salts and glutamic acid and its corresponding alkali metal salts will be obtained from step (a).

Preferably, an aqueous solution of a mixture of alanine and its corresponding alkali metal salt and glutamic acid and its corresponding alkali metal salts may have a total solids content in the range of from 15 to 50%. Preferably, such aqueous solution of a mixture of alanine and its corresponding alkali metal salt and glutamic acid and its corresponding alkali metal salts may have a pH value in the range of from 6 to 12.

Preferably, the aqueous solution obtained from step (a) contains less than 0.5% by weight impurities, the percentage being based on the total solids content of the aqueous solution. Such potential impurities may be one or more of magnesium or calcium salts of inorganic acids. Trace amounts of impurities stemming from the L-alanine or the water used shall be neglected in the further context with the present invention.

In step (b) of the inventive process, a double Strecker synthesis is being carried out by treating the aqueous solution of the mixture of obtained in step (a) with formaldehyde and hydrocyanic acid or alkali metal cyanide. The double Strecker synthesis can be carried out by adding alkali metal cyanide or a mixture from hydrocyanic acid and alkali metal cyanide or preferably hydrocyanic acid and formaldehyde to the aqueous solution obtained in step (a). Alternatively, the aqueous solution obtained in step (a) is first treated with formaldehyde to obtain the corresponding Schiff's base followed by addition of hydrocyanic acid. Said addition of formaldehyde and alkali metal cyanide or preferably hydrocyanic acid can be performed in one or more portions. Formaldehyde can be added as gas or as formalin solution or as paraformaldehyde. Preferred is the addition of formaldehyde as 30 to 35% by weight aqueous solution.

In a particular embodiment of the present invention, step (b) of the inventive process is being carried out at a temperature in the range of from 5 to 80° C., preferably from 10 to 45° C.

In one embodiment of the present invention, step (b) of the inventive process is being carried out at a constant temperature in the above range. In another embodiment, step (b) of the inventive process is being carried using a temperature profile, for example by starting the reaction at 15° C. and allowing then stirring the reaction mixture at 25° C.

In one embodiment of the present invention, step (b) of the inventive process is being carried out at elevated pressure, for example 1.01 to 6 bar. In another embodiment, step (b) of the inventive process is being carried at normal pressure (1 bar).

In one embodiment of the present invention, step (b) of the inventive process is being carried out at a constant pH value, and a base or an acid is being added in order to keep the pH value constant. Preferably, however, the pH value during step (b) is decreasing, and neither base nor acid other than, optionally, HCN is being added. In such embodiments, at the end of step (b), the pH value may have dropped to 2 to 4.

In one embodiment of the present invention, step (b) of the inventive process is being carried out by adding 2.0 to 2.5 equivalents based on moles of amine groups of HCN, preferably 2.0 to 2.3, more preferably 2.0 to 2.1.

In one embodiment of the present invention, step (b) of the inventive process is being carried out by adding 2.0 to 2.5 equivalents based on moles of amine groups of formaldehyde, preferably 2.0 to 2.3, more preferably 2.0 to 2.1.

Step (b) can be performed in any type of reaction vessel that allows the handling of hydrocyanic acid. Useful are, for example, flasks, stirred tank reactors and cascades of two or more stirred tank reactors.

From step (b), an aqueous solution of the L- and/or D-enantiomer of the following two dinitriles of formula (B1) and formula (B2) and their corresponding alkali metal salts are obtained, briefly also referred to as dinitriles (B1) and (B2) or alkali metal salt of dinitrile (B1) and (B2), respectively.

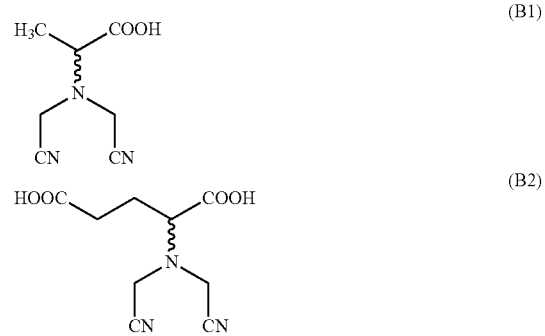

In a preferred embodiment of step (c), the dinitriles resulting from step (b) will be saponified in two steps (c1) and (c2) at different temperatures. In another preferred embodiment stoichiometric amounts of hydroxide or an excess of 1.01 to 1.5 moles of hydroxide per molar sum of COOH groups and nitrile groups of dinitrile of step (b), preferably 1.01 to 1.2 moles, are employed.

Different temperature means in the context of step (c) that the average temperature of step (c1) is different from the average temperature of step (c2). Preferably, step (c1) is being performed at a temperature lower than step (c2). Even more preferably, step (c2) is being performed at an average temperature that is at least 80 K higher than the average temperature of step (c1). Hydroxide in the context of step (c) refers to alkali metal hydroxide, preferably potassium hydroxide and even more preferably to sodium hydroxide.

Step (c1) can be started by adding the solution resulting from step (b) to an aqueous solution of alkali metal hydroxide or adding an aqueous solution of alkali metal hydroxide to a solution resulting from step (b). In another embodiment, the solution resulting from step (b) and an aqueous solution of alkali metal hydroxide are being added simultaneously to a vessel.

When calculating the stoichiometric amounts of hydroxide to be added in step (c1), the sum of COOH groups and nitrile groups from the total theoretical amount of dinitriles (B1) and (B2) are is calculated and the amounts of alkali already present from step (a) and, optionally, step (b), is subtracted.

Step (c1) can be performed at a temperature in the range of from 10 to 80° C., preferable 30 to 65° C. In the context of step (c1) "temperature" refers to the average temperature.

As a result of step (c1), an aqueous solution of the respective diamides and their respective alkali metal salts can be obtained, M being alkali metal. Said solution may also contain corresponding monoamides and/or its mono-, di-, or tri-alkali metal salt.

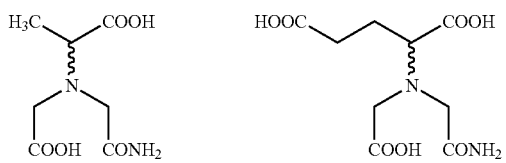 [SMILES: CC(C(=O)O)N(CC(N)=O)CC(=O)O ; NC(=O)CN(CC(=O)O)C(CCC(=O)O)C(=O)O]

Step (c2) can be performed at a temperature in the range of from 90 to 195° C., preferably 175 to 195° C. In the context of step (c2) "temperature" refers to the average temperature.

In one embodiment of the present invention, step (c2) has an average residence time in the range of from 15 to 360 minutes.

In preferred embodiments the higher range of the temperature interval of step (c2) such as 190 to 195° C. is combined with a short residence time such as 15 to 25 minutes, or the lower range of the temperature interval of step (c2) such as 90° C. to 110° C. is combined with a longer residence time such as 200 to 360 minutes, or a middle temperature such as 185° C. is combined with a middle residence time such as 20 to 45 minutes.

Step (c2) can be performed in the same reactor as step (c1), or—in the case of a continuous process—in a different reactor.

In one embodiment of the present invention step (c2) is carried out with an excess of base of 1.01 to 1.2 moles of hydroxide per mole of nitrile group.

Depending on the type of reactor in which step (c2) is being performed, such as an ideal plug flow reactor, the average residence time can be replaced by the residence time.

In one embodiment of the present invention, step (c1) is being carried out in a continuous stirred tank reactor and step (c2) is being carried out in a second continuous stirred tank reactor. In a preferred embodiment, step (c1) is being carried out in a continuous stirred tank reactor and step (c2) is being carried out in a plug flow reactor, such as a tubular reactor.

In one embodiment of the present invention, step (c1) of the inventive process is being carried out at elevated pressure, for example at 1.05 to 6 bar. In another embodiment, step (c1) of the inventive process is being carried at normal pressure.

Especially in embodiments wherein step (c2) is being carried out in a plug flow reactor, step (c2) may be carried out at elevated pressure such as 1.5 to 40 bar, preferably at least 20 bar. The elevated pressure may be accomplished with the help of a pump or by autogenic pressure elevation.

Preferably, the pressure conditions of steps (c1) and (c2) are combined in the way that step (c2) is carried out at a higher pressure than step (c1).

During step (c2), a partial racemization takes place. Without wishing to be bound by any theory, it is likely that racemization takes place on the stage of the above L-di-amides or of L-MGDA resp. L-GLDA.

In one embodiment of the present invention, the inventive process may comprise steps other than steps (a), (b) and (c) disclosed above. Such additional steps may be, for example, one or more decolourization steps, for example with acti- vated carbon or with peroxide such as $H_2O_2$, or by UV irradiation or combinations of at least two of the foregoing.

A further step other than step (a), (b) or (c) that is preferably carried out after step (c2) is stripping with nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

In embodiments wherein an inventive solution is desired, the solution obtained from step (c2) is just cooled down and, optionally, concentrated by partially removing the water. If dry samples of inventive mixtures are required, the water can be removed by spray drying or spray granulation.

The inventive process may be carried out as a batch process, or as a semi-continuous or continuous process.

In one embodiment, the product obtained at the end of step (c) has a solids content in the range of from 40 to 70% by weight, preferably 45 to 65% by weight, more preferably 48 to 55% by weight.

In one embodiment of the present invention the product obtained at the end of step (c) contains a mixture of L- and D-enantiomers of MGDA or its respective mono-, di- or tri-alkali metal or mono-, di- or tri-ammonium salt or mixtures thereof containing predominantly the respective L-isomer with an enantiomeric excess (ee) in the range of from 10 to 95%, preferably 25 to 90%, more preferably 40 to 85%, most preferably 50 to 75%, and L- and D-enantiomers of GLDA or its respective mono-, di-, tri-, or tetra-alkali metal or mono-, di-, tri- or tetra-ammonium salt or mixtures thereof.

A further aspect of the present invention is the use of an inventive mixture or an inventive solution for the manufacture of laundry detergent compositions and of detergent compositions for cleaners. A further aspect is a process for manufacture of laundry detergents and of detergent compositions cleaners by using an inventive mixture or an inventive solution. Depending on whether a mixing in aqueous formulation or in dry matter is desired, and depending on whether a liquid or solid detergent composition is desired, an inventive aqueous solution or an inventive mixture of isomers can be used. Mixing can be performed by formulation steps known per se.

In particular when mixing is being carried out with an inventive solution for the production of a solid laundry detergent compositions or a solid detergent composition for cleaners, such use is advantageous because it allows to add only reduced amounts of water to be removed later, and it allows for great flexibility because no additional ingredients such as polymer, surfactants or salts are present that otherwise reduce flexibility of the detergent manufacturer.

In one embodiment of the present invention, inventive aqueous solutions may be used as such for the manufacture of laundry detergent compositions or for detergent compositions for cleaners. In other embodiments, inventive aqueous solutions may be used in fully or preferably partially neutralized form for the manufacture of laundry detergent compositions or for detergent compositions for cleaners. In one embodiment, inventive aqueous solutions may be used in fully or preferably partially neutralized form for the manufacture of laundry detergent compositions or of detergent compositions for cleaners, said neutralization being performed with an inorganic acid (mineral acid). Preferred inorganic acids are selected from $H_2SO_4$, HCl, and $H_3PO_4$. In other embodiments, inventive aqueous solutions may be used in fully or preferably partially neutralized form for the manufacture of laundry detergent compositions or of detergent compositions for cleaners, said neutralization being performed with an organic acid. Preferred organic acids are selected from $CH_3SO_3H$, acetic acid, propionic acid, and citric acid.

In the context of the present invention, the term "detergent composition for cleaners" includes cleaners for home care and for industrial or institutional applications. The term "detergent composition for cleaners" includes compositions for dishwashing, especially hand dishwash and automatic dishwashing and ware-washing, and compositions for hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for cleaners are percentages by weight and refer to the total solids content of the detergent composition for cleaner.

In one embodiment of the present invention, laundry detergent compositions according to the present invention may contain in the range of from 1 to 30% by weight of inventive mixture. Percentages refer to the total solids content of the respective laundry detergent composition.

In one embodiment of the present invention, detergent compositions for cleaners according to the present invention may contain in the range of from 1 to 50% by weight of inventive mixture, preferably 5 to 40% by weight and even more preferably 10 to 25% by weight. Percentages refer to the total solids content of the respective detergent composition for home care.

Particularly advantageous laundry detergent compositions and of detergent compositions for cleaners, especially for home care may contain one or more complexing agent other than MGDA and GLDA. Advantageous detergent compositions for cleaners and advantageous laundry detergent compositions may contain one or more complexing agent (in the context of the present invention also referred to as sequestrant) other than a mixture according to the present invention. Examples for sequestrants other than a mixture according to the present invention are IDS (iminodisuccinate), citrate, phosphonic acid derivatives, for example the disodium salt of hydroxyethane-1,1-diphosphonic acid ("HEDP"), and polymers with complexing groups like, for example, polyethyleneimine in which 20 to 90 mole-% of the N-atoms bear at least one $CH_2COO^-$ group, and their respective alkali metal salts, especially their sodium salts, for example IDS-$Na_4$, and trisodium citrate, and phosphates such as STPP (sodium tripolyphosphate). Due to the fact that phosphates raise environmental concerns, it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range of from 10 ppm to 0.2% by weight, determined by gravimetry.

Advantageous detergent compositions for cleaners and advantageous laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (I)

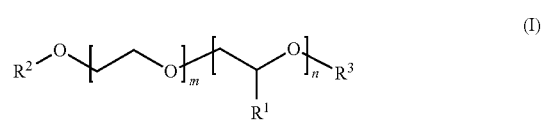

in which the variables are defined as follows:
$R^1$ is identical or different and selected from hydrogen and linear $C_1$-$C_{10}$-alkyl, preferably in each case identical and ethyl and particularly preferably hydrogen or methyl,
$R^2$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^3$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
m and n are in the range of from zero to 300, where the sum of n and m is at least one, preferably in the range of from 3 to 50. Preferably, m is in the range of from 1 to 100 and n is in the range of from 0 to 30.

In one embodiment, compounds of the general formula (I) may be block copolymers or random copolymers, preference being given to block copolymers.

Other preferred examples of alkoxylated alcohols are, for example, compounds of the general formula (II)

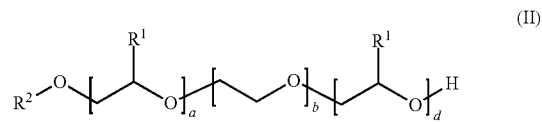

in which the variables are defined as follows:
$R^1$ is identical or different and selected from hydrogen and linear $C_1$-$C_0$-alkyl, preferably identical in each case and ethyl and particularly preferably hydrogen or methyl,
$R^4$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$,
a is a number in the range of from zero to 10, preferably from 1 to 6,
b is a number in the range of from 1 to 80, preferably from 4 to 20,
d is a number in the range of from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (III)

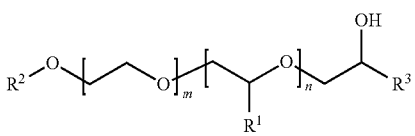
(III)

in which the variables are defined as follows:

$R^1$ is identical or different and selected from hydrogen and linear $C_1$-$C_{10}$-alkyl, preferably in each case identical and ethyl and particularly preferably hydrogen or methyl, $R^2$ is selected from 08-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^3$ is selected from $C_1$-$C_{18}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The integers m and n are in the range of from zero to 300, where the sum of n and m is at least one, preferably in the range of from 5 to 50. Preferably, m is in the range of from 1 to 100 and n is in the range of from 0 to 30.

Compounds of the general formula (II) and (III) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched 08-$C_{14}$-alkyl polyglycosides such as compounds of general average formula (IV) are likewise suitable.

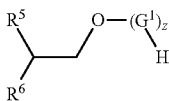
(IV)

wherein:

$R^5$ is $C_1$-$C_4$-alkyl, in particular ethyl, n-propyl or isopropyl, $R^6$ is —$(CH_2)_2$—$R^5$, $G^1$ is selected from monosaccharides with 4 to 6 carbon atoms, especially from glucose and xylose, z in the range of from 1.1 to 4, z being an average number, Further examples of non-ionic surfactants are compounds of general formula (V) and (VI)

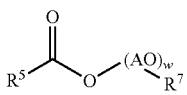
(V)

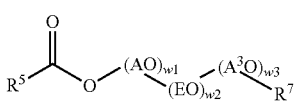
(VI)

AO is selected from ethylene oxide, propylene oxide and butylene oxide,

EO is ethylene oxide, $CH_2CH_2$—O, $R^7$ selected from $C_8$-$C_{18}$-alkyl, branched or linear $A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DEA 198 19 187.

Mixtures of two or more different nonionic surfactants may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (VII)

$$R^8R^9R^{10}N{\rightarrow}O \qquad (VII)$$

wherein $R^{10}$, $R^8$ and $R^9$ are selected independently from each other from aliphatic, cycloaliphatic or $C_2$-$C_4$-alkylene $C_{10}$-$C_{20}$-alkylamido moieties. Preferably, $R^{10}$ is selected from $C_8$-$C_{20}$-alkyl or $C_2$-$C_4$-alkylene $C_{10}$-$C_{20}$-alkylamido and $R^8$ and $R^9$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearoic acid, oleic acid, palmitic acid, ether carboxylates, and alkylether phosphates.

Preferably, laundry detergent compositions contain at least one anionic surfactant.

In one embodiment of the present invention, laundry detergent compositions may contain 0.1 to 60% by weight of at least one surfactant, selected from anionic surfactants, amphoteric surfactants and amine oxide surfactants.

In one embodiment of the present invention, detergent compositions for cleaners may contain 0.1 to 60% by weight of at least one surfactant, selected from anionic surfactants, amphoteric surfactants and amine oxide surfactants.

In a preferred embodiment, detergent compositions for cleaners and especially those for automatic dishwashing do not contain any anionic surfactant.

Detergent compositions for cleaners and laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Detergent compositions for cleaners and laundry detergent compositions may comprise, for example, in the range of from 3 to 10% by weight of chlorine-containing bleach.

Detergent compositions for cleaners and laundry detergent compositions may comprise one or more bleach catalysts. Bleach catalysts can be selected from bleach-boosting transition metal salts or transition metal complexes such as, for example, manganese-, iron-, cobalt-, rutheniumor molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Detergent compositions for cleaners and laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Detergent compositions for cleaners and laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, detergent compositions for cleaners and laundry detergent compositions comprise in total in the range of from 0.1 to 1.5% by weight of corrosion inhibitor.

Detergent compositions for cleaners and laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha$-$Na_2Si_2O_5$, $\beta$-$Na_2Si_2O_5$, and $\delta$-$Na_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range of from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-$\alpha$-olefin, a mixture of $C_{20}$-$C_{24}$-$\alpha$-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly (propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methyl propanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Detergent compositions for cleaners and laundry detergent compositions according to the invention may comprise, for example, in the range of from in total 10 to 70% by weight, preferably up to 50% by weight, of builder. In the context of the present invention, MGDA and GLDA are not counted as builder.

In one embodiment of the present invention, detergent compositions for cleaners and laundry detergent compositions according to the invention may comprise one or more cobuilders.

Detergent compositions for cleaners and laundry detergent compositions may comprise one or more antifoams, selected for example from silicone oils and paraffin oils.

In one embodiment of the present invention, detergent compositions for cleaners and laundry detergent compositions comprise in total in the range of from 0.05 to 0.5% by weight of antifoam.

Detergent compositions for cleaners and laundry detergent according to the invention may comprise one or more enzymes. Examples of enzymes are lipases, hydrolases, amylases, proteases, cellulases, esterases, pectinases, lactases and peroxidases.

In one embodiment of the present invention, detergent compositions for cleaners and laundry detergent compositions according to the present invention may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, detergent compositions for cleaners and laundry detergent compositions according to the invention comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range of from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range of from 10 nm to 100 μm, preferably 100 nm to 5 μm, determined for example by X-ray scattering.

Zinc salt may be present in those detergent compositions for home which are liquid at room temperature in dissolved or in solid or in colloidal form.

In one embodiment of the present invention, detergent compositions for cleaners and laundry detergent compositions comprise in total in the range of from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, detergent compositions for cleaners and laundry detergent compositions according to the invention are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range of from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metals" are deemed to be all metals with a specific density of at least 6 g/cm$^3$ with the exception of zinc. In particular, the heavy metals are metals such as bismuth, iron, copper, lead, tin, nickel, cadmium and chromium.

Preferably, detergent compositions for cleaners and laundry detergent compositions according to the invention comprise no measurable fractions of bismuth compounds, i.e. for example less than 1 ppm.

In one embodiment of the present invention, detergent compositions according to the present invention comprise one or more further ingredient such as fragrances, dyestuffs, organic solvents, buffers, disintegrants for tabs, and/or acids such as methanesulfonic acid.

In one embodiment of the present invention, detergent composition according to the present invention may be in any suitable physical from, for example powdered and/or granular composition, pearls, tablets, liquid, gels, or combinations thereof.

Another aspect of the present invention is the use of a composition comprising alanine and glutamic acid or their respective salts for the preparation of a mixture or solution containing MGDA and GLDA or their respective salts.

The invention is further illustrated by the following working examples.

WORKING EXAMPLES

General Remarks:

The ee values of MGDA were determined by HPLC using a Chirex 3126 column; (D)-penicillamine, 5 μm, 250×4.6 mm. The mobile phase (eluent) was 0.5 mM aqueous CuSO4-solution. Injection: 10 μl, flow: 1.5 ml/min. Detection by UV light at 254 nm. Temperature: 20° C. Running time was 25 min. The ee value was determined as difference of the area % of the L- and D-MGDA peak divided by the sum of area % of L- and D-MGDA peak. Sample preparation: A 10 ml measuring flask was charged with 5 mg of test material and then filled mark with the eluent and then homogenized.

Specific rotation was determined at 20° C., wavelength 589 nm, with a modular circular polarimeter MCP 300, Fa. Anton Paar GmbH.

Viscosities have been measured using a Brookfield viscometer measuring the samples at 23° C. with spindle 31.

Optical appearance has been measured 24 hours after preparation of the aqueous solution, which was stored at 23° C. in a closed bottle.

The following substances were used:

GLDA-$Na_4$ (Dissolvine GL-47 ST™, AkzoNobel Functional Chemicals BV, 47% by weight aqueous solution). The ee of Dissolvine GL-47 ST™ is 95%. Specific rotation of Dissolvine GL-47 S™ is 6.9 deg ml $g^{-1}$ $dm^{-1}$.

The ee values are given in mol-%. All other percentages refer to weight percentages unless specified otherwise.

EXAMPLE 1.1

Synthesis of a Solution of Partially Neutralized L-alanine bis-acetonitrile (ABAN) and L-glutamic Acid amino diacetonitrile sodium Salts (GLDN), Steps (a.1) and (b.1)

Step (a.1): A 1-litre stirred flask was charged at room temperature with 136 g of de-ionized water. 66.88 g of L-alanine (99%, 0.74 mole) were added. To the resultant slurry 39 g of 50% by weight aqueous sodium hydroxide solution (0.49 mole) and 108.62 (99%, 0.57 mole) L-monosodium-glutamate monohydrate were added. After complete addition the slurry was stirred at 50 C for 30 minutes. A clear solution was obtained.

Step (b.1): A 1.5-litre stirred flask was charged with 100 ml of water at room temperature. Then, 350 g of the amino acid solution (1.31 mole) according to step (a.1), 275.4 g of 30% by weight aqueous formaldehyde solution (2.09 mole) and 58.9 g of hydrogen cyanide (99%, 2.17 mole) were added simultaneously at 18 to 20° C. within 60 minutes. The resulting solution was then simultaneously added to a 1.5-litre flask together with additional 14.9 g of hydrogen cyanide (99%, 0.54 mole) at 18 to 20° C. within 60 minutes. Upon completion of the addition the reaction mixture was stirred for additional 30 minutes at 20° C. A solution was obtained that contained partially neutralized L-alanine bis-acetonitrile (ABAN) and L-glutamic acid amino diacetonitrile (GLDN) sodium salt.

EXAMPLE 1.2

Syntheses of an Aqueous Solution of MGDA-$Na_3$ and GLDA-$Na_4$ (c1.1) and (c2.1)

Step (c1.1): A 1.5-litre stirred flask was charged with 100 ml of water and 29.2 g of 50% by weight aqueous sodium hydroxide solution (0.37 moles) and heated to 30 C. Then, simultaneously 900 g of the solution of partially neutralized ABAN and GLDN of Example 1 and 263 g of 50% by weight aqueous sodium hydroxide solution (3.29 moles) were added dropwise. An exothermic reaction could be observed. The reaction mixture was stirred for 2 hours.

Step (c2.1): The reaction mixture obtained according to (c1.1) was stirred at 80-90° C. for 6 hours. The color of the reaction mixture turned to light yellow. The $NH_3$ formed during the reaction was continuously removed by stripping. The volume of the reaction mixture was kept constant by repeated addition of water.

A 40% solution of MGDA-$Na_3$ and GLDA-$Na_4$ was so obtained. The overall yield was 96%, determined by titration of Fe(III+) in the form of $FeCl_3$ in aqueous solution. The individual yields were 96% MGDA-$Na_3$ (ee>96%) and 92% GLDA-$Na_4$ (ee>96%) with 0.06% nitrilotriacetic acid (NTA)-$Na_3$ and 0.30% glutamic acid N-monoacetic acid (GLMA)-$Na_3$ as determined by HPLC analysis.

The resulting aqueous solution was concentrated to 57% by weight and stable at least for 3 months.

Example 2

Step (a.2) was performed in accordance with step (a.1) in Example 1.1.

The continuous syntheses of ca. 40% solutions of inventive solutions were carried out in cascade of 6 stirred tank reactors, total volume of 8.5 l. The reaction mixture passed all 6 stirred tank reactors (STR.1 to STR.6) consecutively. The last stirred tank reactor to be passed, STR.6, was connected to a tubular reactor, TR.7. In the first three stirred tank reactors, STR.1 to STR.3, partially neutralized mixture of ABAN and GLDN were synthesized, and STR.1 to STR.3 were operated at 20° C. The average residence time in STR.1 to STR.3 was 45 to 90 min in total. In the three stirred tank reactors STR.4 to STR.6 the saponification was carried out. STR.4 to STR.6 were operated at 60° C. The average residence time in STR.4 to STR.6 was 170 to 400 min in total. The saponification was then completed in tubular reactor TR.7 which was operated with a temperature of 180° C. The pressure in TR.7 was 22 bar, and the residence time was 31 minutes. The final ammonia stripping was done in a column under normal pressure using steam. Formaldehyde (30% aqueous solution), an aqueous solution of L-alanine (I) and its sodium salt, L-Glutamate obtained according to 1, step (a.2), and 80 mole-% of the required HCN were added to STR.1, the remaining 20% of the required HCN were added to STR.2, the required sodium hydroxide solution was added in STR.4.

The molar ratios of the feed materials were as follows:
L-alanine and the alkali metal salt: 0.56, L-Na-glutamate: 0.44

Formaldehyde=1.95 to 2.07,
HCN=1.95 to 2.10 and
Sodium hydroxide=3.15 (including sodium hydroxide added in step (a.2).

A 40% solution of MGDA-$Na_3$ and GLDA-$Na_4$ was so obtained. The overall yield was 95%, determined by titration of Fe(III+) in the form of $FeCl_3$ in aqueous solution. NTA-$Na_3$ was 0.04% and 0.30% GLMA-$Na_3$ as determined by HPLC analysis.

EXAMPLES 3 to 6

Examples 3 to 6 were carried out as described in Examples 1.1 and 1.2. Table 1 summarizes raw materials and process parameters applied. Table 2 summarizes yield and by products.

TABLE 1

Raw materials and process parameters for the manufacture of solutions of $MGDA-Na_3$ and $GLDA-Na_4$ according to Examples 1.1 and 1.2.

| # | Step (b) Temperature | Step (b) Concentrations (Raw materials: L-monosodium glutamate monohydrate, L-alanine (65% neutralized with NaOH) | Step (b) Dosage | Step (c1) NaOH | Steps (c1) and (c2) Saponification |
|---|---|---|---|---|---|
| Example 3 | 19-20° C. | 30% by weight (0.74 moles alaninate, 0.57 moles glutamate) | 1) HCN (2.17 moles) and formaldehyde (2.73 moles) within 60 min. 2) HCN (0.54 moles) within 60 min 3) stirring for 30 min at 19-20° C. | 3.66 moles | Step (c1.3) Dosage of NaOH: 1 h/28-32° C. After-reaction: 1 h/31-35° C. Step (c2.3) 6.5 h/98-100° C. |
| Example 4 | 19-21° C. | 45% by weight (0.74 moles alaninate, 0.57 moles glutamate) | 1) HCN (2.17 moles) and formaldehyde (2.73 moles) within 60 min. 2) HCN (0.54 moles) within 60 min 3) stirring for 30 min at 20° C. | 3.66 moles | Step (c1.4) Dosage of NaOH: 1 h/30° C. After-reaction: 1 h/30° C. Step (c2.4) 7.5 h/92-96° C. |
| Example 5 | 18-23° C. | 50% by weight (0.74 moles alaninate, 0.57 moles glutamate) | 1) HCN (2.17 moles) and formaldehyde (2.75 moles) within 60 min. 2) HCN (0.54 moles) within 60 min 3) stirring for 30 min at 20° C. | 3.74 moles | Step (c1.5) Dosage of NaOH: 1 h/22-32° C. After-reaction: 1.5 h/30° C. Step (c2.5) 5.5 h/80-92° C. |
| Example 6 | 35-40° C. | 30% by weight (0.74 moles alaninate, 0.57 moles glutamate) | 1) Formaldehyde (2.70 moles) within 15 min 2) HCN (2.15 moles) within 30 min at 30° C. 3) HCN (0.54 moles) within 30 min at 40° C. 4) stirring for 60 min at 40° C. | 4.03 moles | Step (c1.6) Dosage of NaOH: 1 h/40-57° C. After-reaction: 1 h/40° C. Step (c2.6) 10 h/90-93° C. |

TABLE 2

Yield and by products.

| # | Yield by Fe(III+) titration [%] | Concentration of active ingredients Fe(III+) titration [% by weight] | $GLDA-Na_4$ (HPLC) [% by weight] | $MGDA-Na_3$ (HPLC) [% by weight] | $NTA-Na_3$ (HPLC) (standardized to 40% by weight solution) [% by weight] | $GLMA-Na_3$ (HPLC) (standardized to 40% by weight solution) [% by weight] |
|---|---|---|---|---|---|---|
| Example 3 | 93.7 | 39.6 | 19.2 | 18.9 | 0.10 | 0.4 |
| Example 4 | 97.0 | 34.4 | 16.3 | 16.2 | 0.05 | 0.7 |
| Example 5 | 95.1 | 39.0 | 19.4 | 20.2 | 0.06 | 0.3 |
| Example 6 | 91.5 | 40.3 | 18.3 | 21.4 | 0.22 | 0.3 |

EXAMPLE 7

A mixture of 125.9 g $MGDA-Na_3$ (40% by weight aqueous solution, ee=37%) and $GLDA-Na_4$ (47% by weight aqueous solution, ee=95%) was prepared.

COMPARATIVE EXAMPLE 1

A mixture of 125.9 g $MGDA-Na_3$ (40% by weight aqueous solution, ee<5%) and $GLDA-Na_4$ (47% by weight aqueous solution, ee<5%) was prepared.

COMPARISON OF EXAMPLES 7 to 9 and Comparative Example 1

Table 3 summarizes the preparation of solutions of $MGDA-Na_3$ and $GLDA-Na_4$ and their concentration to approx. 60% by weight by evaporation of water in a rotatory evaporator. The solutions have been diluted by addition of water to 56% by weight and 40% by weight. The properties of the solutions are summarized in Table 4 and Table 5.

TABLE 3

Parameters for the preparation and concentration of mixtures of Examples 7 to 9.

| | | Example 7 | Example 8 | Example 9 | Comparative Example 1 |
|---|---|---|---|---|---|
| $MGDA-Na_3$ (ee 35%) | [g] | 125.9 | | | |
| $GLDA-Na_4$ (ee 95%) | [g] | 105.9 | | | |
| $MGDA-Na_3$ (ee <5%) | [g] | | | | 134.6 |
| $GLDA-Na_4$ (ee <5%) | [g] | | | | 97.0 |
| Example 3 | [g] | | 231.6 | | |
| Example 4 | [g] | | | 235.7 | |
| Total mass | [g] | 231.9 | 231.6 | 235.7 | 231.6 |

TABLE 3-continued

Parameters for the preparation and concentration of mixtures of Examples 7 to 9.

|  |  | Example 7 | Example 8 | Example 9 | Comparative Example 1 |
|---|---|---|---|---|---|
| Water evaporated | [g] | 64.1 | 82.0 | 96.4 | 74.5 |
| Theoretical concentration of total actives (MGDA/GLDA) | [% by weight] | 59.6 | 61.3 | 58.2 | 58.3 |
| Concentration of active ingredients Fe(III+) titration | [% by weight] | 60.4 | 61.4 | 57.2 | 59.5 |

TABLE 4

Properties of solutions diluted 56 to 57% by weight.

|  |  | Example 7 | Example 8 | Example 9 | Comparative Example 1 |
|---|---|---|---|---|---|
| Concentration of active ingredients Fe(III+) titration [% by weight] | [% by weight] | 56.7 | 56.9 | 56.1 | 56.3 |
| Optical appearance |  | clear solution | clear solution | clear solution | clear solution |
| Viscosity measured with Brookfield, 23° C., spindle 31 | [mPas] | 1650 | 1530 | 965 | 1630 |

TABLE 5

Properties of solutions diluted to approx. 40% by weight.

|  |  | Example 7 | Example 8 | Example 9 | Comparative Example 1 |
|---|---|---|---|---|---|
| Concentration of active ingredients Fe(III+) titration | [% by weight] | 40.2 | 40.3 | 40.4 | 40.4 |
| Specific rotation | [deg ml $g^{-1}$ $dm^{-1}$] | 3.3 | 3.9 | 4.0 | 0.6 |

The specific rotation measured by polarimetry is higher for Example 7 to 9 according to the present invention compared to the Comparative Example 1.

The invention claimed is:

1. A process for preparing a composition comprising methyl glycine diacetic acid (MGDA) or its respective mono-, di-, trialkali metal salt or its respective mono-, di- or tri-ammonium salt or mixtures thereof, and glutamic acid diacetic acid (GLDA) or its respective mono-, di-, tri-, or tetra-alkali metal or mono-, di-, tri- or tetra-ammonium salt or mixtures thereof, the process comprising:
   (a) dissolving in water
      (a1) alanine in its L- or D-enantiomeric form or its respective monoalkali metal salt or mixtures thereof, and
      (a2) glutamic acid as L- or D-enantiomer or its respective mono-, or dialkali metal or mixtures thereof,
      wherein a molar ratio (a1) to (a2) of alanine to glutamic acid is in the range of from 1:9 to 9:1, to obtain a mixture;
   (b) converting the mixture with formaldehyde and hydrocyanic acid or alkali metal cyanide to dinitriles; and
   (c) saponifying the dinitriles, to obtain the composition.

2. The process according to claim 1, wherein the saponifying (c) is carried out in two steps (c1) and (c2) at different temperatures.

3. The process according to claim 1, wherein the saponifying (c) is carried out by employing stoichiometric amounts of hydroxide or an excess of 1.01 to 1.5 moles of hydroxide per molar sum of COOH groups and nitrile groups in the converting (b).

4. The process according to claim 1, wherein a solids content of the composition is in the range of from 40 to 70% by weight.

5. The process according to claim 1, wherein the molar ratio of (a1) to (a2) is in the range of from 2.5: 7.5 to 7.5: 2.5.

6. The process according to claim 1, wherein the composition comprises a mixture of L- and D- enantiomers of MGDA or its respective mono-, di- or tri-alkali metal or mono-, di- or tri-ammonium salt or mixtures thereof comprising predominantly the respective L-isomer with an enantiomeric excess (ee) in the range of from 10 to 95%, and L- and D-enantiomers of GLDA or its respective mono-, di-, tri-, or tetra-alkali metal or mono-, di-, tri- or tetra-ammonium salt or mixtures thereof.

7. The process according to claim 1, wherein the saponification (c) is carried out with sodium hydroxide or potassium hydroxide.

8. The process according to claim 1, wherein the converting (b) is carried out at a temperature in the range of 10 to 45° C.

9. The process s according to claim 2, wherein the saponifying (c1) is carried out at a temperature in the range of from 10 to 80° C., and the saponifying (c2) is carried out at a temperature in the range of from 90 to 195° C.

10. The process according to claim 2, wherein the saponifying (c2) has an average residence time in the range of from 15 to 360 minutes.

11. A composition, comprising L- and D- enantiomers of MGDA or its respective mono-, di- or tri-alkali metal or mono-, di- or tri-ammonium salt or mixtures thereof containing predominantly the respective L-isomer with an enantiomeric excess (ee) in the range of from 10 to 95%, and L- and D-enantiomers of GLDA or its respective mono-, di-, tri-, or tetra-alkali metal or mono-, di-, tri- or tetra-ammonium salt or mixtures thereof, wherein:

the composition does not contain an organic polymer; and
the composition does not contain a surfactant.

12. The composition according to claim 11, wherein a molar ratio of MGDA to GLDA or their respective salts is in the range of from 1:9 to 9:1.

13. An aqueous solution, comprising the composition of claim 11, wherein the aqueous solution has a solids content in the range of from 40 to 70% by weight.

14. A solution, comprising MGDA and GLDA, wherein the solution is obtained from a composition formed by the process of claim 1.

15. A composition formed from the aqueous solution of claim 13, said composition being a laundry detergent composition or a detergent composition for cleaners.

* * * * *

UNITED STATES PATENT AND TRADEMARK OFFICE
CERTIFICATE OF CORRECTION

PATENT NO. : 10,619,125 B2
APPLICATION NO. : 15/554466
DATED : April 14, 2020
INVENTOR(S) : Constanze Franzke et al.

It is certified that error appears in the above-identified patent and that said Letters Patent is hereby corrected as shown below:

On the Title Page

Column 2, item [57], Abstract, Line 7, "com-prises" should read -- comprises --.

In the Specification

Column 1, Line 15, "tetraammonium" should read -- tetra-ammonium --;
    Line 24, "tetraammonium" should read -- tetra-ammonium --;
    Line 47, "tetraammonium" should read -- tetra-ammonium --.

Column 4, Line 55, "carboxymethylalanin" should read -- carboxymethylalanine --.

Column 5, Line 42, "polyvinylpyrolidone." should read -- polyvinylpyrrolidone. --.

Column 12, Line 3, "non-ionic" should read -- nonionic --;
    Line 5, "non-ionic" should read -- nonionic --;
    Lines 45-50, should read --  --.

Column 12, Line 53, "$C_1$-$C_0$" should read -- $C_1$-$C_{10}$ --.

Column 13, Line 14, "08-$C_{22}$-" should read -- $C_8$-$C_{22}$ --;
    Line 34, "08-$C_{14}$-" should read -- $C_8$-$C_{14}$- --;
    Line 51, "non-ionic" should read -- nonionic --.

Signed and Sealed this
Twenty-fifth Day of August, 2020

Andrei Iancu
*Director of the United States Patent and Trademark Office*

CERTIFICATE OF CORRECTION (continued)
U.S. Pat. No. 10,619,125 B2

Column 14, Line 8, "DEA" should read -- DE-A --;
    Line 47, "stearoic" should read -- stearic --.

Column 15, Line 7, "chlorosulfamide," should read -- chlorosulfonamide, --;
    Line 19, "rutheniumor" should read -- ruthenium- or --.

Column 17, Line 29, "g/l" should read -- g/1 --.

Column 19, Line 14, "ST™" should read -- S™ --;
    Line 16, "ST™" should read -- S™ --.

Columns 21-22, Table 1, Line 5, "(Raw" should read -- Raw --.